(12) United States Patent
Liu et al.

(10) Patent No.: US 9,656,359 B1
(45) Date of Patent: May 23, 2017

(54) DEVICES AND SYSTEMS FOR LENS SUPPORT

(71) Applicant: Verily Life Sciences LLC, Mountain View, CA (US)

(72) Inventors: Zenghe Liu, Alameda, CA (US); Daniel Patrick Barrows, Sunnyvale, CA (US); Jeffrey George Linhardt, Pleasanton, CA (US)

(73) Assignee: Verily Life Sciences, LLP, Mountain View, CA (US)

( * ) Notice: Subject to any disclaimer, the term of this patent is extended or adjusted under 35 U.S.C. 154(b) by 414 days.

(21) Appl. No.: 14/109,214

(22) Filed: Dec. 17, 2013

(51) Int. Cl.
| | |
|---|---|
| *B23Q 3/08* | (2006.01) |
| *G02C 7/04* | (2006.01) |
| *G02C 7/02* | (2006.01) |
| *G02C 11/00* | (2006.01) |
| *G02C 7/08* | (2006.01) |
| *A61B 5/145* | (2006.01) |
| *A61B 5/00* | (2006.01) |
| *B29D 11/00* | (2006.01) |

(52) U.S. Cl.
CPC ............... *B23Q 3/08* (2013.01); *G02C 7/04* (2013.01); *G02C 7/049* (2013.01); *A61B 5/14532* (2013.01); *A61B 5/6821* (2013.01); *B29D 11/00125* (2013.01); *G02C 7/022* (2013.01); *G02C 7/083* (2013.01); *G02C 11/10* (2013.01); *G02C 2202/16* (2013.01)

(58) Field of Classification Search
CPC .......... B23Q 3/08; B23Q 3/088; A61B 3/125; A61B 5/6821; A61B 5/14532; G02C 7/049; G02C 7/14; G02C 7/04; G02C 2202/16; G02C 11/10; G02C 7/083; G02C 7/022; B24B 13/005; B29L 2011/0041; B29D 11/00125; B29D 11/0807; B29D 11/00038
USPC ........... 269/20; 51/159.73; 264/2.6, 1.1, 2.5; 425/808; 351/159.73, 159.02, 159.03
See application file for complete search history.

(56) References Cited

U.S. PATENT DOCUMENTS

| | | | |
|---|---|---|---|
| 5,005,633 A * | 4/1991 | Mathews | B23Q 1/54 164/334 |
| 6,224,467 B1 | 5/2001 | Tanaka et al. | |
| 7,241,125 B2 | 7/2007 | Dubey et al. | |
| 8,985,763 B1 * | 3/2015 | Etzkorn | G02C 11/00 351/159.02 |
| 2003/0024829 A1 * | 2/2003 | Matsuzawa | A61L 2/18 206/5.1 |

(Continued)

*Primary Examiner* — Larry E Waggle, Jr.
*Assistant Examiner* — Mahdi H Nejad
(74) *Attorney, Agent, or Firm* — McDonnell Boehnen Hulbert & Berghoff LLP (57) ABSTRACT

An apparatus may include a mounting structure configured to removably mount a concave surface of a device. The mounting structure may have a convex mounting surface that corresponds to the concave surface of the device. The device may have a convex surface opposite the concave surface. The apparatus may also include a base structure that has a flat surface. The apparatus may also include a support structure coupled to the base structure and the mounting structure. The support structure may be configured to align the mounting structure at a given angle such that a target area on the convex surface of the device is substantially parallel to the flat surface of the base structure when the device is mounted on the mounting structure.

20 Claims, 8 Drawing Sheets

(56) References Cited

U.S. PATENT DOCUMENTS

| | | | | |
|---|---|---|---|---|
| 2007/0001328 A1* | 1/2007 | Kelly | ............... | B29D 11/00134 |
| | | | | 264/1.32 |
| 2011/0062607 A1* | 3/2011 | Clements | ........... | B29D 11/0023 |
| | | | | 264/2.6 |
| 2011/0257930 A1* | 10/2011 | Gourraud | .............. | B24B 13/005 |
| | | | | 702/150 |
| 2012/0218508 A1* | 8/2012 | Pugh | ................ | B29D 11/00028 |
| | | | | 351/159.01 |
| 2013/0235334 A1* | 9/2013 | Widman | .......... | B29D 11/00144 |
| | | | | 351/159.6 |
| 2013/0235339 A1* | 9/2013 | Widman | .......... | B29D 11/00038 |
| | | | | 351/159.73 |
| 2014/0268019 A1* | 9/2014 | Riall | ....................... | G02C 7/047 |
| | | | | 351/159.04 |
| 2014/0371560 A1* | 12/2014 | Etzkorn | ................. | A61B 5/682 |
| | | | | 600/365 |
| 2015/0077663 A1* | 3/2015 | Pugh | ...................... | G02C 7/083 |
| | | | | 349/13 |
| 2015/0148774 A1* | 5/2015 | Yao | .................... | A61M 5/1723 |
| | | | | 604/504 |
| 2015/0327764 A1* | 11/2015 | Graham | ................. | G02C 7/049 |
| | | | | 351/219 |
| 2015/0328740 A1* | 11/2015 | Gacoin | .............. | B24B 13/0055 |
| | | | | 451/5 |
| 2016/0259180 A1* | 9/2016 | Liu | .......................... | G02C 7/04 |

* cited by examiner

DEVICES AND SYSTEMS FOR LENS SUPPORT

BACKGROUND

Unless otherwise indicated herein, the materials described in this section are not prior art to the claims in this application and are not admitted to be prior art by inclusion in this section.

An eye-mountable device may be configured to monitor health-related information based on at least one analyte detected in a tear film of a user wearing the eye-mountable device. For example, the eye-mountable device may be in the form of a contact lens that includes a sensor configured to detect the at least one analyte (e.g., glucose). The eye-mountable device may also be configured to monitor various other types of health-related information.

SUMMARY

In one example, an apparatus is provided that comprises a mounting structure configured to removably mount a concave surface of a device. The mounting structure may have a convex mounting surface that corresponds to the concave surface of the device. The device may have a convex surface opposite the concave surface. The apparatus further comprises a base structure that has a flat surface. The apparatus further comprises a support structure coupled to the base structure and the mounting structure. The support structure may be configured to align the mounting structure at a given angle such that a target area on the convex surface of the device is substantially parallel to the flat surface of the base structure when the device is mounted on the mounting structure.

In another example, a method is provided that comprises mounting a concave surface of a device on a convex mounting surface of a mounting structure. The mounting structure may be coupled to a support structure at a given angle. The device may have a convex surface opposite the concave surface. The method further comprises aligning a target area on the convex surface of the device such that the target area is substantially parallel to a flat surface of a base structure that is also coupled to the support structure. The aligning may be based on the device being mounted on the convex mounting surface of the mounting structure and the mounting structure being coupled to the support structure at the given angle.

In yet another example, a system is provided that comprises a device having a concave surface and a convex surface opposite the concave surface. The system further comprises a mounting structure configured to removably mount the concave surface of the device. The mounting structure may have a convex mounting surface that corresponds to the concave surface of the device. The system further comprises a base structure that has a flat surface. The system further comprises a support structure coupled to the base structure and the mounting structure. The support structure may be configured to align the mounting structure at a given angle such that a target area on the convex surface of the device is substantially parallel to the flat surface of the base structure when the device is mounted on the mounting structure.

These as well as other aspects, advantages, and alternatives, will become apparent to those of ordinary skill in the art by reading the following detailed description, with reference where appropriate to the accompanying figures.

DETAILED DESCRIPTION

The following detailed description describes various features and functions of the disclosed systems and methods with reference to the accompanying figures. In the figures, similar symbols identify similar components, unless context dictates otherwise. The illustrative system, device and method embodiments described herein are not meant to be limiting. It may be readily understood by those skilled in the art that certain aspects of the disclosed systems, devices and methods can be arranged and combined in a wide variety of different configurations, all of which are contemplated herein.

A body-mountable device such as an ophthalmic device (e.g., an eye-mountable device or implantable medical device) may include embedded electronics configured to perform various functions such as taking measurements or communicating with an external device. For example, an eye-mountable device such as a contact lens may include circuitry situated on a substrate embedded in transparent material of the eye-mountable device.

In some examples, the transparent material may be in the form of a round lens with a concave surface, which can be removably mounted on a corneal surface overlaying a pupil of an eye, and a convex surface, which faces outward, away from the eye, when the concave surface is mounted on the corneal surface. In some examples, the substrate may be embedded near the periphery of the transparent material to avoid interference with incident light received closer to a central region of the eye. In some examples, the convex surface may include a channel in the transparent material configured to allow analytes in tear to reach a sensor on the substrate that is embedded in the transparent material when the eye-mountable device is mounted on the eye. For example, the sensor may obtain a reading related to an analyte concentration (e.g., a glucose concentration) in liquid entering the channel.

Within examples herein, devices, methods and systems are provided for supporting a device during testing and/or fabrication. An example apparatus may include a mounting structure configured to removably mount a concave surface of a device. For example, the mounting structure may correspond to a lens holder configured to support a concave surface of an eye-mountable device. The mounting structure may have a convex mounting surface that corresponds to the concave surface of the device. The device may have a convex surface opposite the concave surface. The apparatus may further include a base structure that has a flat surface. The apparatus may further include a support structure coupled to the base structure and the mounting structure. The support structure may be configured to align the mounting structure at a given angle such that a target area on the convex surface of the device is substantially parallel to the flat surface of the base structure.

In one example, the device may be an eye-mountable device that has a channel in the transparent material that is aligned with the sensor embedded in the eye-mountable device. In this example, liquid deposition while the device is mounted to the apparatus may be performed on the target area that is substantially parallel to the flat surface such that the liquid does not flow away on the convex surface of the device due to gravity. For example, a reagent layer may be deposited while the device is mounted to sensitize the sensor to a given analyte. For example, a layer of glucose oxidase ("GOX") may be deposited around a working electrode of the sensor to catalyze reaction of glucose into hydrogen peroxide ($H_2O_2$). The hydrogen peroxide may then be oxidized at the working electrode to release electrons to the working electrode that generate a current that can be measured by the eye-mountable device to determine glucose concentration. Thus, for example, the apparatus may facilitate depositing a liquid solution to form the reagent layer during fabrication of the device.

Figure 1A:
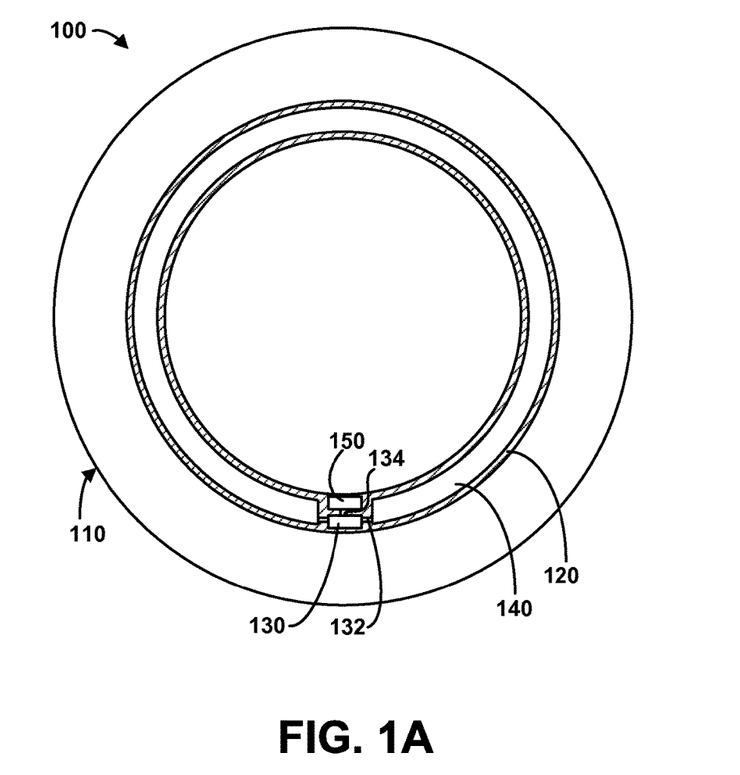
FIG. 1A is a top view of an example eye-mountable device, according to an example embodiment.
Figure 1B:
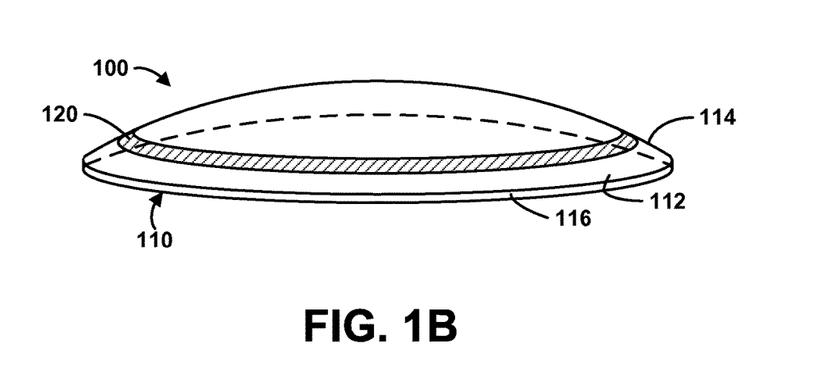
FIG. 1B is a side view of the example eye-mountable device shown in FIG. 1A, according to an example embodiment.

Referring now to the figures, FIG. 1A is a top view of an example eye-mountable device 100, according to an example embodiment. FIG. 1B is a side view of the example eye-mountable device shown in FIG. 1A, according to an example embodiment. It is noted that the relative dimensions in FIGS. 1A and 1B are not necessarily to scale, but have been rendered for purposes of explanation only in describing the arrangement of the example eye-mountable device 100. The eye-mountable device 100 may be formed of a transparent material 110 shaped as a curved disk. The transparent material 110 may allow incident light (e.g., field of view of the eye) to be transmitted to the eye while the eye-mountable device 100 is mounted to the eye. In some examples, the transparent material 110 may be a biocompatible polymeric material similar to those employed to form vision correction and/or cosmetic contact lenses in optometry, such as polyethylene terephthalate (PET), polymethyl methacrylate (PMMA), polyhydroxyethylmethacrylate (polyHEMA), silicone hydrogels, combinations of these, etc. The transparent material 110 may be formed with one side having a concave surface 112 suitable to fit over a corneal surface of the eye. The opposite side of the disk may have a convex surface 114 configured to not interfere with eyelid motion while the eye-mountable device 100 is mounted to the eye. A circular outer side edge 116 may connect the concave surface 112 and the convex surface 114.

The eye-mountable device 100 may have dimensions similar to vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 100 can be selected according to the size and/or shape of the corneal surface of a wearer's eye.

The transparent material 110 may be formed with a curved shape in a variety of ways. For example, techniques similar to those employed to form vision-correction contact lenses, such as heat molding, injection molding, spin casting, etc. may be employed to form the transparent material 110. When the eye-mountable device 100 is mounted to an eye, the convex surface 114 faces outward to an ambient environment while the concave surface 112 faces inward, toward the corneal surface. The convex surface 114 may therefore be considered an outer, top surface of the eye-mountable device 100 whereas the concave surface 112 may be considered an inner, bottom surface. The "top" view shown in FIG. 1A is facing the convex surface 114.

A substrate 120 may be embedded in the transparent material 110. In some examples, the substrate 120 may be embedded along an outer periphery of the transparent material 110, away from a central region of the eye-mountable device 100. Thus, in these examples, the substrate 120 does not interfere with vision because it is too close to the eye to be in focus and is positioned away from the central region where ambient light is transmitted to eye-sensing portions of the eye. In some examples, the substrate 120 may be formed of a second transparent material to further mitigate effects on visual perception.

The substrate 120 may be shaped as a flat, circular ring (e.g., a disk with a centered hole). The flat surface of the substrate 120 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. In some examples, the substrate 120 and the transparent material 110 may be substantially cylindrically symmetric about a common central axis. The substrate 120 may have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. In some examples, the substrate 120 may be implemented in a variety of different form factors.

A controller 130, loop antenna 140, and sensor 150 may be disposed on a side of the substrate 130 that is facing the convex surface 114 ("top side") of the transparent material 110 as shown in FIG. 1A. However, in some embodiments, the controller 130, the loop antenna 140, and/or the sensor 150 may be disposed on any side of the substrate 120. For example, the controller 130 may be disposed in the opposite side ("bottom side") of the substrate 120 that is facing the concave surface 112 of the transparent material 110. In some examples, one or more components disposed on the substrate 120 may be disposed on a side of the substrate 120 that is facing the circular outer side edge 116 of the transparent material 110. The controller 130 may include logic elements configured to operate the loop antenna 140 and the sensor 150. The controller 130 may be electrically connected to the loop antenna 140 by interconnects 132 also situated on the substrate 120. Similarly, the controller 130 may be electrically connected to the sensor 150 by an interconnect 134. In some examples, the interconnects 132, 134, the loop antenna 140, and any conductive electrodes (e.g., for the sensor 150, etc.) may be formed from conductive materials patterned on the substrate 120 by a process such as deposition or lithography. The conductive materials patterned on the substrate 120 may be, for example, gold, platinum, titanium, carbon, aluminum, copper, silver, silver-chloride, and/or other metals.

The loop antenna 140 may be formed as a layer of conductive material patterned along a flat surface of the substrate 120 to form a flat conductive ring. In some examples, the loop antenna 140 may be formed without making a complete loop. For example, the loop antenna 140 may have a cutout to allow room for the controller 130 and the sensor 150, as illustrated in FIG. 1A. In some examples, the loop antenna 140 may also be arranged as a continuous strip of conductive material that wraps entirely around the flat surface of the substrate 120 one or more times. Thus, in this example, interconnects 132 between the ends of such a wound antenna (e.g., antenna leads) may then be passed through the substrate 120 to the controller 130.

The sensor 150 may include a bio-sensor such as a glucose sensor configured to measure a concentration of an analyte (e.g., in saliva, in tear fluid, etc.). Additionally or alternatively, the sensor 150 may include other sensors such as temperature sensor, humidity sensor, pressure sensor, or any other sensor configured to provide a reading to the controller 130. In one example scenario, the sensor 150 may provide the reading to the controller 130, and the controller 130 may provide the reading to an external device via the loop antenna 140.

Although not illustrated in FIGS. 1A-1B, in some examples, the substrate 120 may include additional components such as light sources, photovoltaic cells, additional sensors, and/or other electronic components that the controller 130 is configured to operate. In some examples, the loop antenna 140 may be configured to harvest energy from incident radio frequency radiation on the eye-mountable device 100. In some examples, the loop antenna 140 may be replaced by, or supplemented with a photovoltaic cell (e.g., solar cells) configured to harvest the energy from ambient light surrounding the eye-mountable device 100 and/or receive a modulated light signal from an external device.

Figure 1C:
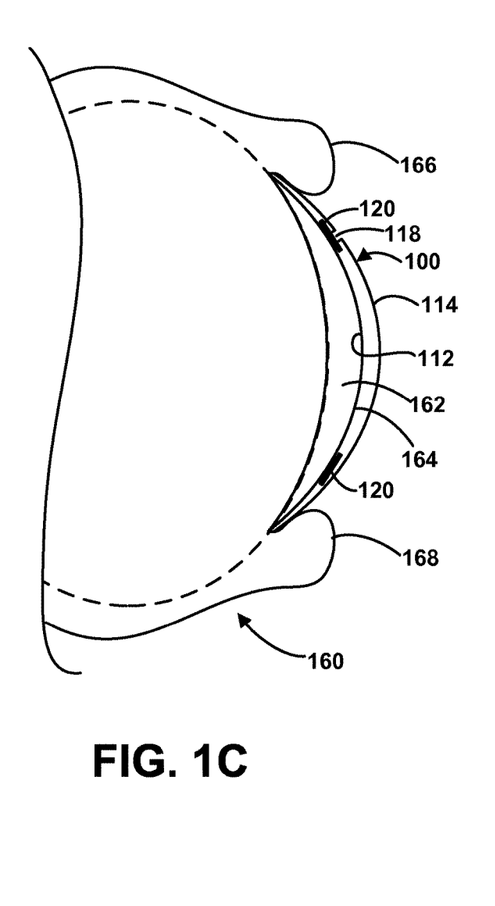
FIG. 1C is a side cross-section view of the example eye-mountable device shown in FIGS. 1A and 1B while mounted to a corneal surface of an eye, according to an example embodiment.
Figure 1D:
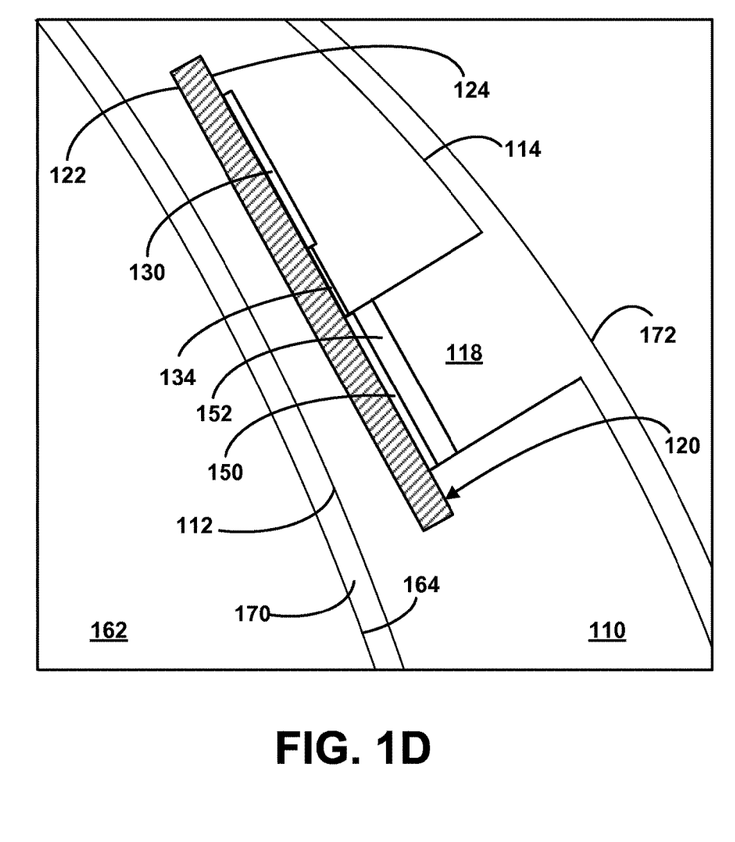
FIG. 1D is a close-in side cross-section view enhanced to show the substrate in the example eye-mountable device when mounted as shown in FIG. 1C, according to an example embodiment.

FIG. 1C is a side cross-section view of the example eye-mountable device 100 shown in FIGS. 1A and 1B while mounted to a corneal surface 164 of an eye 160, according to an example embodiment. FIG. 1D is a close-in side cross-section view enhanced to show the substrate 120 in the example eye-mountable device 100 when mounted as shown in FIG. 1C, according to an example embodiment. It is noted that relative dimensions in FIGS. 1C and 1D are not necessarily to scale, but have been rendered for purposes of explanation only in describing the arrangement of example eye-mountable electronic device 100. For example, thickness of the eye-mountable device 100 may be about 200 micrometers, while thickness of tear film layers 170, 172 may each be about 10 micrometers, although this ratio is may not be reflected in the drawings. Some aspects are exaggerated to allow for illustration and facilitate explanation.

The eye 160 includes a cornea 162 that is covered by bringing an upper eyelid 166 and a lower eyelid 168 together over the eye 160. Incident light may be received by the eye 160 through the cornea 162, where light is optically directed to light sensing elements of the eye 160 (e.g., rods and cones, etc.) to stimulate visual perception. The motion of the eyelids 166, 168 may distribute a tear film across the exposed corneal surface 164 of the eye 160. The tear film may include an aqueous solution secreted by the lacrimal gland to protect and lubricate the eye 160, for example. When the eye-mountable device 100 is mounted on the eye 160, the tear film may coat both the concave surface 112 and the convex surface 114, respectively, with an inner layer 170 (along the concave surface 112) and an outer layer 172 (along the convex layer 114). The tear film layers 170, 172 may be about 10 micrometers in thickness and together account for about 10 microliters, for example.

As shown in the cross-sectional views in FIGS. 1C and 1D, the substrate 120 may be inclined such that the flat mounting surfaces of the substrate 120 are approximately parallel to the adjacent portion of the convex surface 114. As described above, the substrate 120 may be a flattened ring with an inward-facing surface 122 (facing the concave surface 112 of the transparent material 110) and an outward-facing surface 124 (facing the convex surface 114).

As shown in FIG. 1D, the sensor 150, the controller 130, and the conductive interconnect 134 are mounted on the outward-facing surface 134 such that the sensor 150 is facing the convex surface 114. However, in some examples, the sensor 150 may be mounted on the inward-facing surface 122 of the substrate 120 such that the sensor 150 is facing the concave surface 112. With this arrangement, for example, the sensor 150 may receive analyte concentrations in the tear film 172 through a channel 118 in the transparent material 110 as shown in FIG. 1D.

The eye-mountable device 100 illustrates an example device that has the concave surface 112 opposite the convex surface 114. In some examples, a liquid may be deposited on the convex surface 114 of the eye-mountable device 100 during fabrication and/or testing of the eye-mountable device 100. As illustrated in FIG. 1D, for example, a reagent layer 152 may be included in the eye-mountable device 100 proximally to the sensor 150 to sensitize the sensor to a given analyte. For example, the liquid may deposited via the channel 118 during fabrication of the eye-mountable device 100 to form the reagent layer 152. For example, the liquid may comprise a mixture or solution that includes a reagent. In this example, the solvent may evaporate such that the reagent layer 152 remains on the sensor 150. Alternatively, for example, the layer may comprise the reagent in a liquid state (e.g., at a high temperature) such that the reagent layer 152 is formed when the reagent cools down. In some examples, the reagent layer 152 may comprise a layer of glucose oxidase ("GOX") situated around a working electrode of the sensor 150 to catalyze reaction of glucose in the tear film 172 into hydrogen peroxide ($H_2O_2$). The hydrogen peroxide may then be oxidized at the working electrode to release electrons that generate an electric current, for example, as illustrated below.

$$H_2O_2 \longrightarrow 2\,H^+ + O_2 + 2\,e^-$$

Further, for example, the generated electric current by either reduction or oxidation reactions may be approximately proportionate to a reaction rate of the reaction illustrated above. In some examples, the reaction rate may correspond to the analyte concentration (e.g., glucose concentration), and thus the generated electric current may provide an indication of the analyte concentration. For example, the generated electric current may be measured by the controller 130 via interconnects 134 and the controller 130 may then determine the analyte concentration.

In one example, the liquid may include a test solution with a known analyte concentration that is deposited on the reagent layer 152 via the channel 118 to validate the reading provided by the sensor 150. In another example, the liquid may include a fluid configured to form the channel 118 and/or other structures in the transparent material 110. In yet another example, the liquid may correspond to a fabrication material for patterning interconnects 132, 134, the loop antenna 120 and/or other components on the substrate 120. In these examples and the example of fabricating the reagent layer 152, depositing such liquid on a target area in the convex surface 114 may cause the liquid to flow away on the convex surface 114 due to gravity instead of reaching the target area. For example, where the liquid is the reagent (e.g., glucose oxidase), the liquid may flow away on the convex surface 114 instead of reaching the sensor 150 via the channel 118 to form the reagent layer 152.

Additionally or alternatively, in some examples, components in the eye-mountable device 100 such as the controller 130, interconnects 132, 134, and/or the loop antenna 140 may be observed by a microscope or computer vision system to verify/validate functionality of the eye-mountable device 100. In these examples, the microscope and/or computer vision system may be configured to view the components in the target area described above. For example, aesthetic appearance of the various components disposed on the substrate 120 may be verified. Additionally, for example, connections between patterned materials such as the interconnects 132, 134, the loop antenna 140 and/or other components such as the controller 130 and the sensor 150 may also be verified similarly.

Within examples, methods and apparatuses are provided to facilitate such liquid deposition and/or such visual verification.

Figure 2:
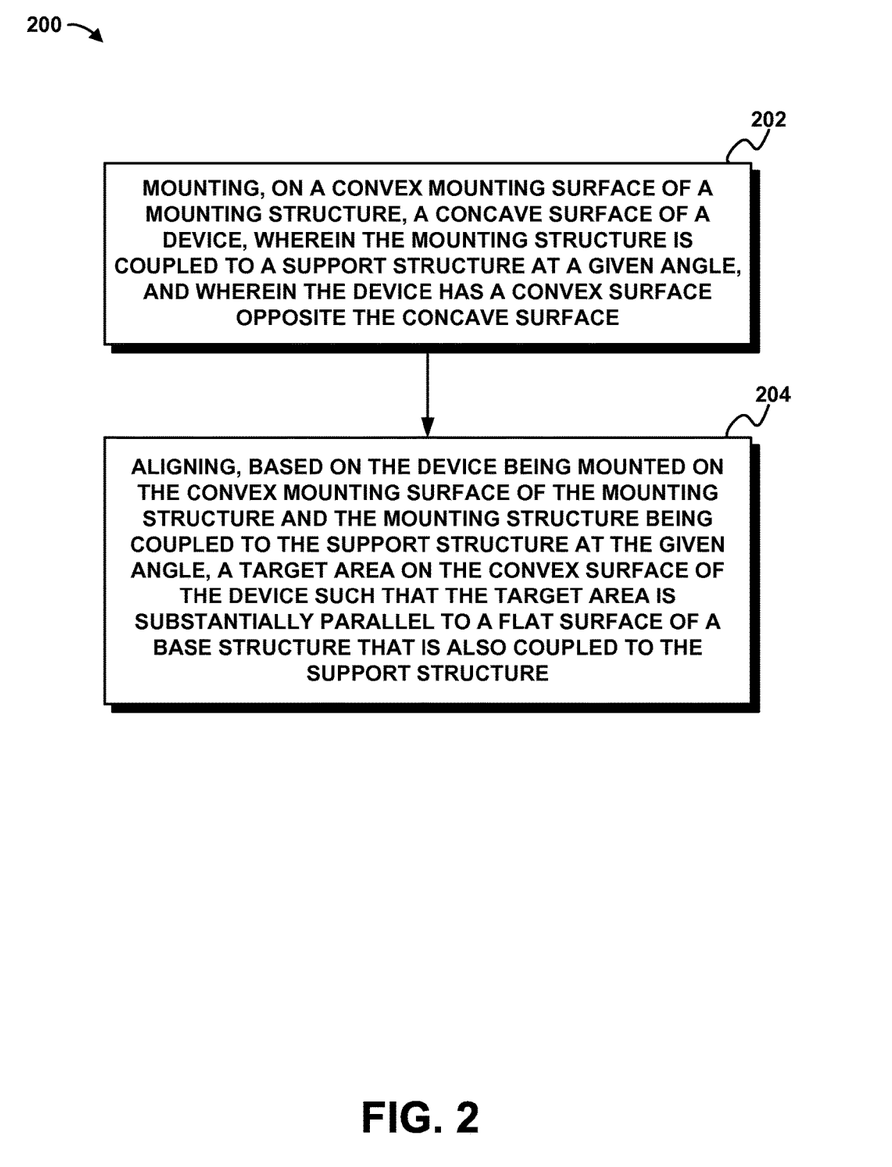
FIG. 2 is a block diagram of an example method for mounting a device to convex mounting surface of a mounting structure, according to an example embodiment.

FIG. 2 is a block diagram of an example method 200 for mounting a device to convex mounting surface of a mounting structure, according to an example embodiment. Method 200 shown in FIG. 2 presents an embodiment of a method that could be used with the device 100, for example. Method 200 may include one or more operations, functions, or actions as illustrated by one or more of blocks 202-204. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the flowchart shows functionality and operation of one possible implementation of present embodiments. In this regard, each block may represent a module, a segment, or a portion of a manufacturing or operation process.

At block 202, the method 200 includes mounting a concave surface of a device on a convex mounting surface of a mounting structure. The mounting structure may be coupled to a support structure at a given angle. The device may have a convex surface opposite the concave surface. For example, the device may be the eye-mountable device 100 of FIG. 1 and the mounting structure may have the convex mounting surface that corresponds to the concave surface 112 of the device 100. Further, for example, the convex mounting surface may have curvature that substantially matches curvature of the concave surface 112 of the device 100.

At block 204, the method 200 includes aligning a target area on the convex surface of the device such that the target area is substantially parallel to a flat surface of a base structure that is also coupled to the support structure. The aligning may be based on the device being mounted on the convex mounting surface of the mounting structure and the mounting structure being coupled to the support structure at the given angle.

For example, the given angle may be selected such that the target area is substantially parallel to the flat surface of the base structure. Thus, for example, liquid deposition of a volume of liquid on the target area may allow the target area to hold the volume of liquid instead of the volume flowing along the convex surface of the device as discussed in the description of FIGS. 1A-1D. For example, the flat surface may be perpendicular to a direction of gravity and thus the target area may also be perpendicular to the direction of gravity when the device is mounted to the mounting structure.

In some examples, the mounting structure may include an alignment mark that corresponds to the target area on the device. Thus, for example, when operating the apparatus, the target area may be aligned based on the alignment mark to cause the target area to be substantially parallel to the flat surface of the base structure.

Figure 3A:
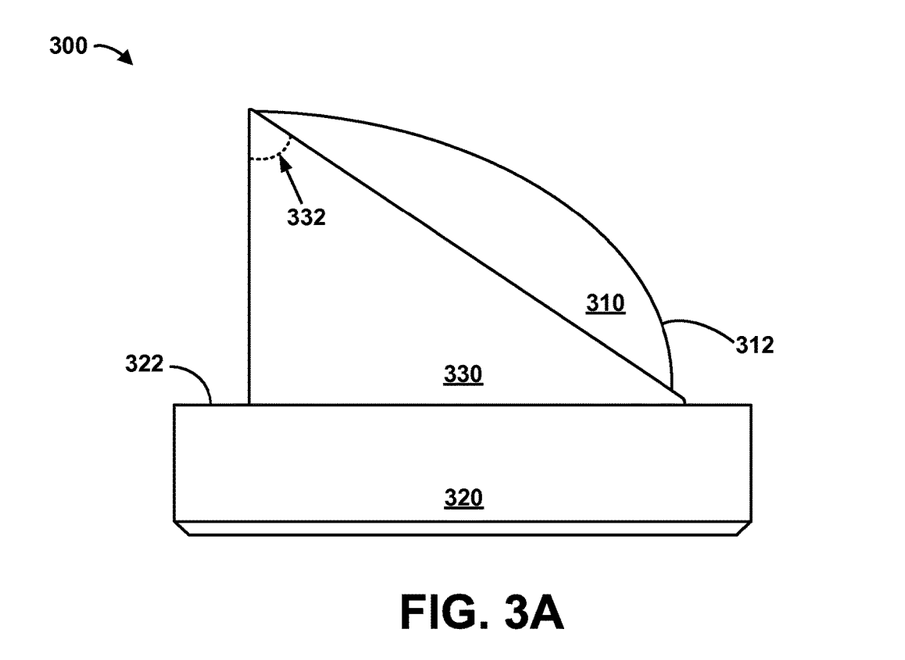
FIG. 3A illustrates an example apparatus that includes a mounting structure, according to an example embodiment.
Figure 3B:
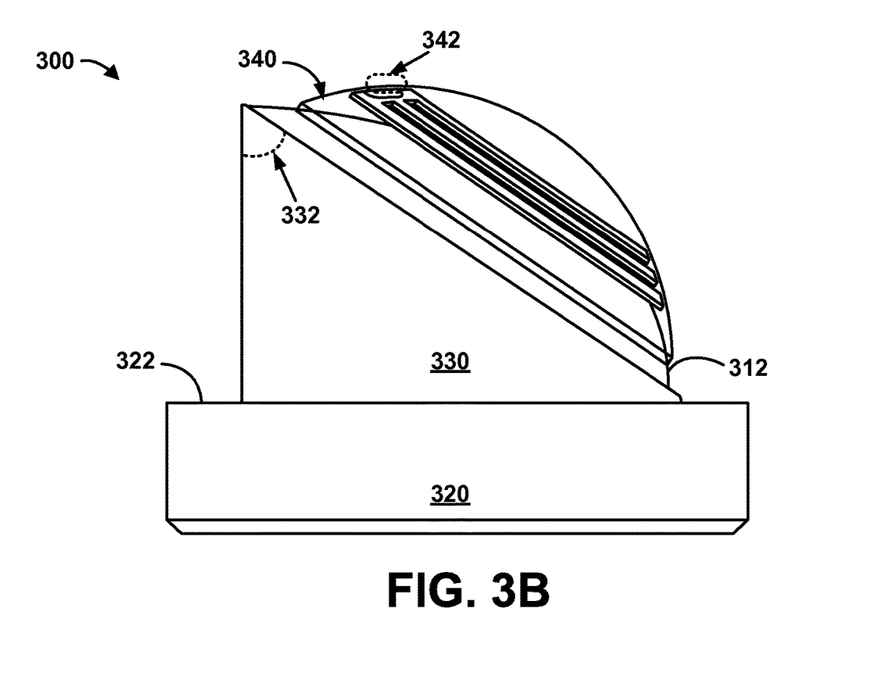
FIG. 3B illustrates the example apparatus of FIG. 3A when a concave surface of a device is mounted on the mounting structure, according to an example embodiment.

FIG. 3A illustrates an example apparatus 300 that includes a mounting structure 310, according to an example embodiment. FIG. 3B illustrates the example apparatus 300 of FIG. 3A when a concave surface of a device 340 is mounted on the mounting structure 310, according to an example embodiment. In some examples, the apparatus 300 may be configured to removably mount a device 340 that is similar to the device 100 of the FIGS. 1A-1D using a method such as the method 200 of FIG. 2. For example, the device 340 may have the concave surface opposite a convex surface similarly to the device 100 of FIG. 1. As illustrated in FIG. 3A, the apparatus 300 includes the mounting structure 310, a base structure 320, and a support structure 330.

The mounting structure 310 may have a convex mounting surface 312 configured to correspond to the concave surface of the device 340. For example, curvature of the convex mounting surface 312 may match curvature of at least a portion of the concave surface of the device 340 as illustrated in FIG. 3B. Thus, for example, the device 340 may be mounted on the mounting structure 310 by placing the concave surface of the device 340 on the convex mounting surface 312 of the mounting structure 310.

As illustrated in FIGS. 3A-3B, the base structure 320 may have a flat surface 322. Further, for example, the support structure 330 may be coupled to the mounting structure 310 and the base structure 320. As illustrated in FIG. 3B, in some examples, the support structure 330 may be configured to align the mounting structure 310 at a given angle 332 such that a target area 342 on the convex surface of the device 340 is substantially parallel to the flat surface 322 of the base structure 320. Although illustrated in FIG. 3B that the target area 342 is in a central region of the convex surface of the device 340, in some examples, the given angle 332 may be configured such that the target area 342 corresponds to a different region of the convex surface of the device 340. For example, the given angle 332 may be selected during fabrication of the apparatus 300 such that the target area 342 corresponds to a region where a given component (e.g., sensor 150 of the device 100) may reside. In some examples, the given angle 332 may correspond to 50°-70°.

In an example scenario, the apparatus 300 may be placed on a horizontal working surface such as a microscope platform or other horizontal platform. Further, in this example, the device 340 may then be mounted on the mounting structure 310 and liquid deposition may be performed on the target area 342. For example, the liquid deposition may comprise depositing a chemical fluid during fabrication of the device 340 (e.g., for etching to form the channel 118 in the device 100). In another example, the liquid deposition may comprise depositing an analyte solution and/or reagent solution onto a sensing area of the device 340 (e.g., to form the reagent layer 152 on the sensor 150 of the device 100). Thus, in some examples, the target area 342 may be configured to hold a volume of liquid when the device 340 is mounted on the mounting structure 310 such that the target area 342 is substantially parallel to the flat surface 322 of the base structure 320.

In some examples, the device 340, when mounted, may remain on the mounting structure 310 due to friction and/or Van der Waals forces between the concave surface of the device 340 and the convex mounting surface 312. Although not illustrated in FIGS. 3A-3B, in some examples, the mounting structure 310 may include an indentation configured to maintain the device 340 in a given position on the mounting structure 310. For example, the indentation may have a shape of a perimeter of the device 340 such that the device 340 fits along the indentation when mounted to the mounting structure 310.

The mounting structure 310, base structure 320, and/or support structure 330 included in the apparatus 300 may be formed from any solid material such as metals (e.g., aluminium, steel, etc.), plastics (e.g., Polyvinyl Chloride (PVC), Polystryrene, Polyamide, etc.), or other solids (e.g., wood, rubber, foam, concrete, glass, etc.). In some examples, the mounting structure 310, base structure 320, and/or support structure 330 may be fabricated as one solid object. For example, the apparatus 300 may be fabricated via an additive manufacturing technique such as three-dimensional (3D) printing. Alternatively, for example, the apparatus 300 may be fabricated via a subtractive manufacturing technique such as traditional machining (e.g., cutting, drilling, etc.). In some examples, the apparatus 300 may be fabricated via other techniques such as molding (e.g., blow molding, compression molding, foam molding, injection molding, thermoforming, etc.) or casting (e.g., sand casting, high pressure die casting, centrifugal casting, etc.).

It is noted that the relative dimensions in FIGS. 3A and 3B are not necessarily to scale, but have been rendered for purposes of explanation only in describing the arrangement of the apparatus 300. For example, a height of the support structure 330 relative to a height of the base structure 320 may be different than the illustration of FIGS. 3A and 3B.

Figure 4:
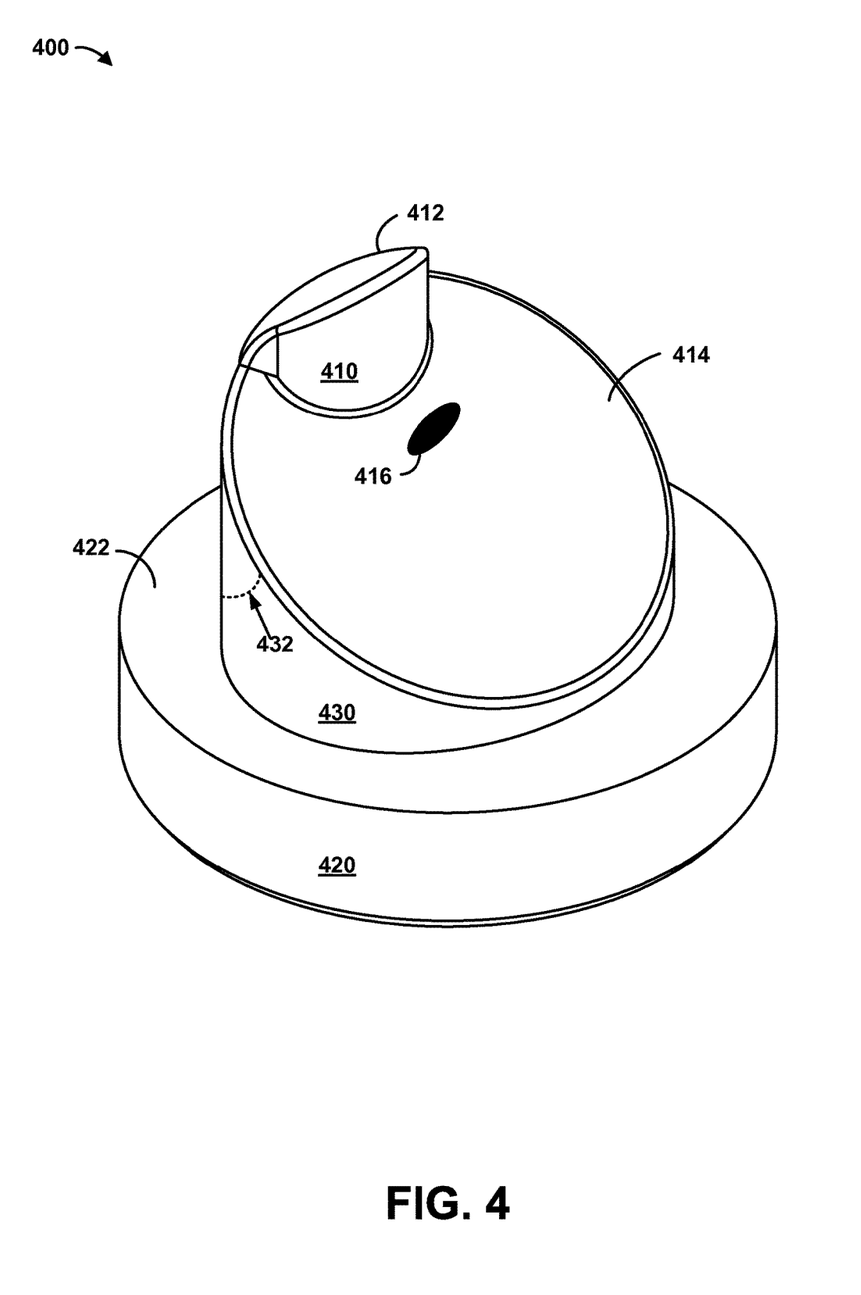
FIG. 4 illustrates an example apparatus that includes a mounting structure having an indentation, according to an example embodiment.

FIG. 4 illustrates an example apparatus 400 that includes a mounting structure 410 having an indentation 414, according to an example embodiment. In some examples, the apparatus 400 may be configured to removably mount a device such as the device 100 of the FIGS. 1A-1D using a method such as the method 200 of FIG. 2. The structure and operation of the apparatus 400 may be similar to the apparatus 300 of FIG. 3. For example, the apparatus 400 includes a mounting structure 410, a base structure 420, and a support structure 430 similar, respectively, to the mounting structure 310, the base structure 320, and the support structure 330 of the apparatus 300.

Additionally, for example, the mounting structure 410 includes a convex mounting surface 412 configured to removably mount at least a portion of a concave surface of a device such as the device 340 of FIG. 3, similarly to the convex mounting surface 312. The support structure 430 may be configured to align the mounting structure 410 at a given angle 432 similarly to the given angle 332 of the apparatus 300. For example, when a device such as the device 340 of FIG. 3 is mounted to the apparatus 400, a target area on a convex surface of the device opposite the concave surface may be substantially parallel to a flat surface 422 based on the given angle 432. Additionally, in some examples, the composition of the apparatus 400 may be similar to the apparatus 300 of FIG. 3. For example, the apparatus 400 may be formed from a plastic material via a process such as 3D printing or plastic molding.

As illustrated in FIG. 4, the mounting structure 410 includes an indentation 414. In some examples, the indentation 414 may correspond to an omitted portion of the mounting structure 410. Referring back to FIGS. 3A-3B, the mounting structure 410 may include the convex mounting surface 412 that has a similar curvature to a corresponding portion of the convex mounting surface 312 of the mounting structure 310. However, for example, a portion of the mounting structure 310 may be omitted to form the indentation 414 and the mounting structure 410.

Thus, for example, when a device such as the device 340 of FIG. 3B is mounted on the convex mounting surface 412, a portion of the concave surface of the device may reside and correspond to the convex mounting surface 412. In this example, the mounted device may remain on the convex mounting surface 412 due to friction and/or Van der Waals forces between the mounted device and the convex mounting surface 412 even when a portion of the concave surface of the device does not reside on the convex mounting surface 412. Additionally, for example, the indentation 414 may be configured to accommodate a support for supporting the concave surface of the device during mounting and unmounting of the device. For example, a tool such as a lens tool may be utilized to mount and/or unmount the device on the mounting structure 410 and the indentation 414 may accommodate space for the tool.

In some examples, a shape of the indentation 414 may be configured to align with a shape of one or more features in the removably mounted device. For example, an edge between the indentation 414 and the convex mounting surface 412 may correspond to a shape of a component on the device such that matching the edge with the shape of the component may facilitate mounting the device at a given position and/or orientation.

As mentioned earlier, in some examples, friction and/or van der Waals forces may maintain the mounted device on the mounting structure 410. Additionally, in some examples, the indentation 414 may be configured to reduce such friction and van der Waals forces between the device and the mounting structure 410 when the device is mounted. Referring back to the example of FIGS. 3A-3B, a large contact area between the concave surface of the device 340 and the mounting structure 310 may cause changing a position or orientation of the device 340 when mounted to be difficult, for example. In the apparatus 400, for example, such forces may be reduced due to reducing a corresponding contact area between the concave surface of the mounted device and the mounting structure 410. Thus, for example, in apparatus 400, changing a given position and/or orientation of a mounted device may be less difficult than a corresponding change in the apparatus 300.

As illustrated in FIG. 4, the mounting structure 410 may also include an alignment mark 416. In some examples, the alignment mark 416 may correspond to a target area on a convex surface of a mounted device that is substantially parallel to the flat surface 422 when the device is mounted. For example, referring back to FIG. 3B, the target area may correspond to the target area 342, and thus, an operator of the apparatus 400 may align a portion of the device 340 when mounted on the mounting structure 410 based on the alignment mark 416 such that the target area 342 of the device 340 corresponds to the portion of the device 340 where liquid deposition may happen. Alternatively, in some examples, the target area may correspond to the convex mounting surface 412. For example, the indentation 414 may be configured such that the convex mounting surface 412 corresponds to a location where a target area on a convex surface of a mounted device may be substantially parallel to the flat surface 422.

Figure 5A:
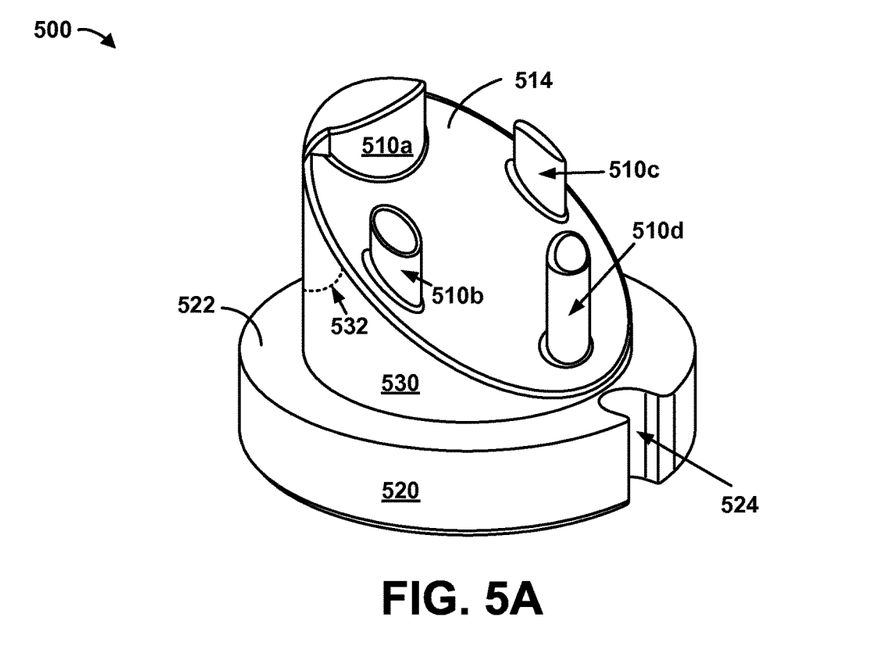
FIG. 5A illustrates another example apparatus that includes mounting structures having indentations, according to an example embodiment.
Figure 5B:
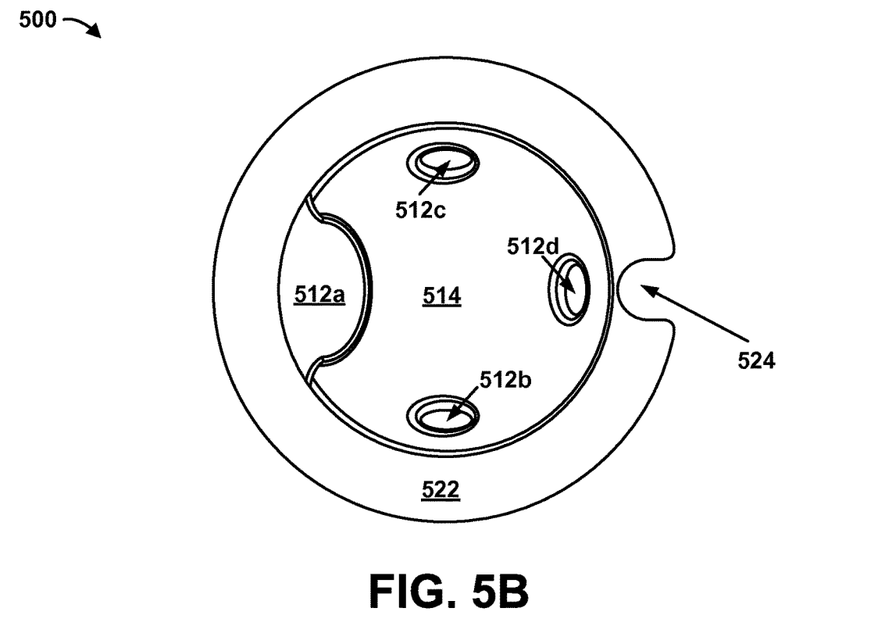
FIG. 5B illustrates a top view of the example apparatus of FIG. 5A, according to an example embodiment.

FIG. 5A illustrates another example apparatus 500 that includes mounting structures 510a-d having an indentation 514, according to an example embodiment. FIG. 5B illustrates a top view of the example apparatus 500 of FIG. 5A, according to an example embodiment. In some examples, the apparatus 500 may be configured to removably mount a device such as the device 100 of the FIGS. 1A-1D using a method such as the method 200 of FIG. 2. The structure, operation, and composition of the apparatus 500 may be similar to the apparatus 300 of FIG. 3. For example, the apparatus 500 includes the mounting structures 510a-d, a base structure 520, and a support structure 530 similar, respectively, to the mounting structure 310, the base structure 320, and the support structure 330 of the apparatus 300.

Additionally, for example, the mounting structures 510a-d include convex mounting surfaces 512a-d configured to removably mount at least a portion of a concave surface of a device such as the device 340 of FIG. 3, similarly to the convex mounting surface 312. The support structure 530 may be configured to align the mounting structures 510a-d at a given angle 532 similarly to the given angle 332 of the apparatus 300. For example, when a device such as the device 340 of FIG. 3 is mounted to the apparatus 500, a target area on a convex surface of the device opposite the concave surface may be substantially parallel to a flat surface 522 based on the given angle 532. Similarly to the apparatus 400 of the FIG. 4, in some examples, indentation 514 may correspond to an omitted portion of a spherical surface that corresponds to the concave surface of the device. For example, the spherical surface may correspond to the convex mounting surface 312 of FIGS. 3A-3B, and the indentation 514 may correspond to an omitted portion of the mounting structure 310 such that the convex mounting surfaces 512a-d have a curvature that corresponds to a portion of the concave surface of the removably mounted device.

Additionally, in some examples, the indentation 514 may be configured to accommodate a support for mounting and/or unmounting a device such as the device 100 of FIGS. 1A-1D. Additionally, for example, the indentation 514 may reduce friction and/or van der Waals forces between the mounted device and convex mounting surfaces 512a-d similarly to the indentation 414 of FIG. 4. As illustrated in FIGS. 5A-5B, the convex mounting surfaces 512a-d may correspond to at least a portion of the concave surface of the mounted device to facilitate the mounting and/or unmounting of the device and provide support for the device when mounted.

The base structure 520 may also include a cavity 524 configured to facilitate placement of the apparatus 500 in a given orientation. For example, the cavity 524 may be configured receive a ridge at a given position such that the apparatus 500 is at the given orientation when the ridge is received by the cavity. For example, the ridge may be included in an assembly belt that is aligned with a liquid dropping apparatus such that the target area corresponds to a position of liquid dropped by the liquid dropping apparatus when the cavity 524 receives the ridge (e.g., when the apparatus 500 is mounted).

Figure 6:
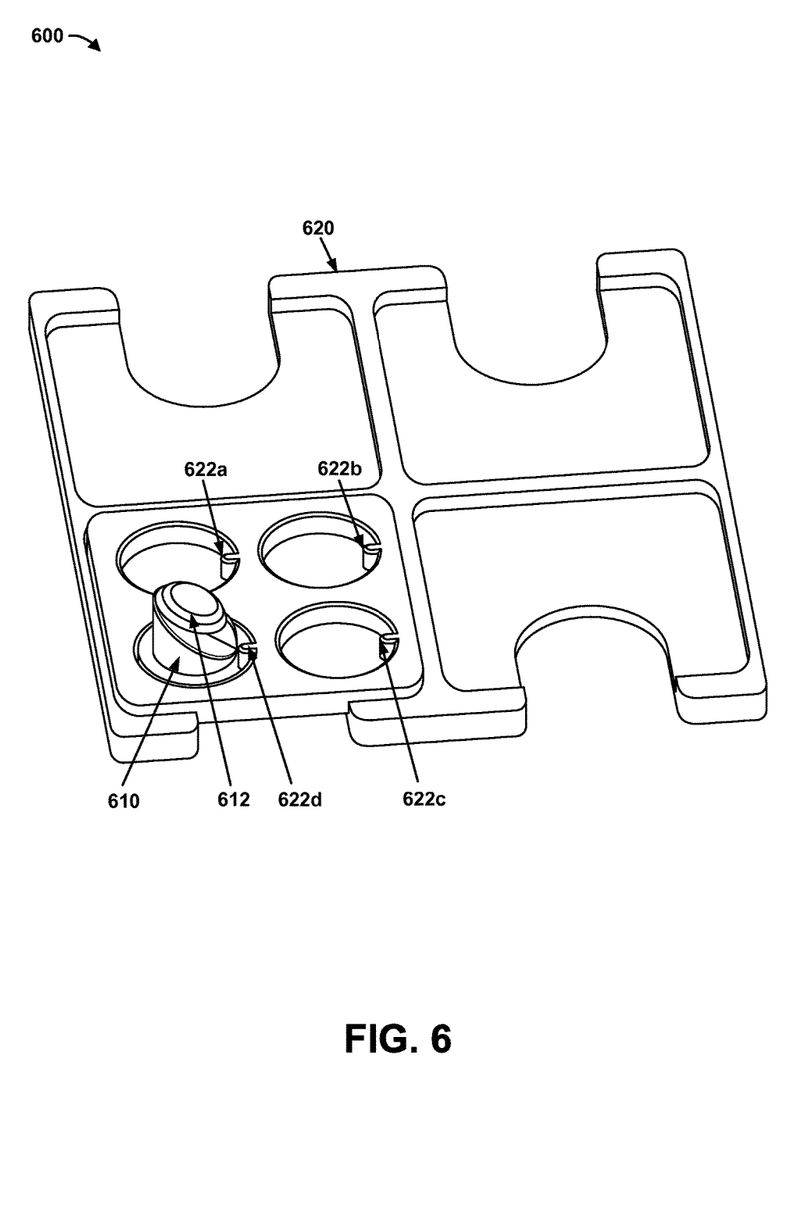
FIG. 6 illustrates an example system for holding an apparatus in a given orientation, according to an example embodiment.

FIG. 6 illustrates an example system 600 for holding an apparatus 610 in a given orientation, according to an example embodiment. The system 600 may be utilized to hold the apparatus 610 that may be similar to the apparatuses 300-500, for example. Further, as illustrated in FIG. 6, the apparatus 610 includes a device 612 mounted on the apparatus 610, similarly to the device 340 of the apparatus 300 in FIG. 3B. In some examples, a target area on a convex surface of the device 612 may be substantially parallel to a flat surface of a base structure of the apparatus 610 as described in the embodiments of the apparatuses 300-500.

The system 600 may include a holder 620 configured to hold the apparatus 610 in the given orientation. In some examples, the holder 620 may comprise a tray under a microscope, or other apparatus configured to removably mount the apparatus 610 in the given orientation. For example, the holder 620 may be arranged under a liquid dropping apparatus such that liquid drops from the liquid dropping apparatus are received on the target area of the device 612 based on the given orientation of the apparatus 610 when the apparatus 610 is mounted on the holder 620.

In some examples, the holder 620 may be configured to mount more than one apparatus such as the apparatus 610. For example, as illustrated in FIG. 6, the holder 620 includes ridges 622a-d configured to align the more than one apparatus in the given orientation. For example, the ridge 622d may be received by a cavity in the base structure of the apparatus 610 similar to the cavity 524 of the apparatus 500 in the FIGS. 5A-5B. Thus, for example, when the base structure of the apparatus 610 is mounted to the holder 620, the ridge 622d may be received by the cavity of the base structure to align the apparatus 610 in the given orientation.

Figure 7A:
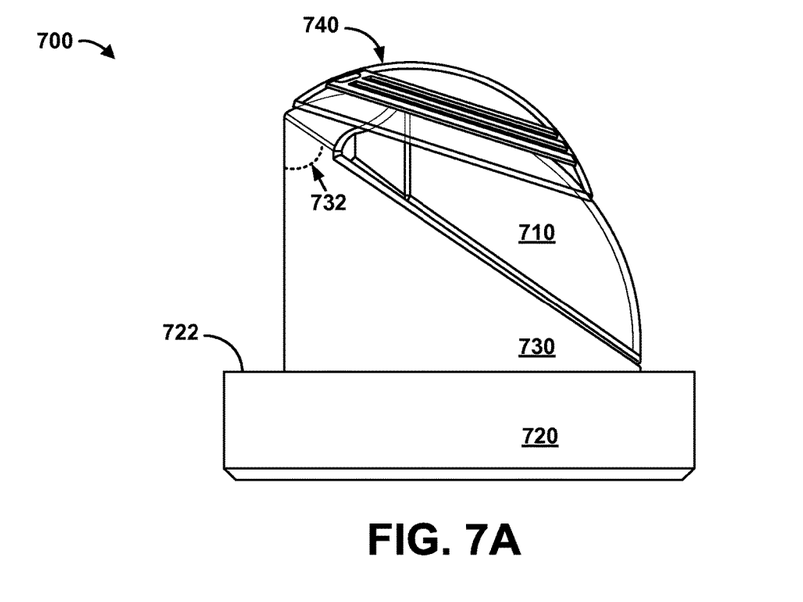
FIG. 7A illustrates yet another example apparatus that includes a mounting structure having an indentation, according to an example embodiment.
Figure 7B:
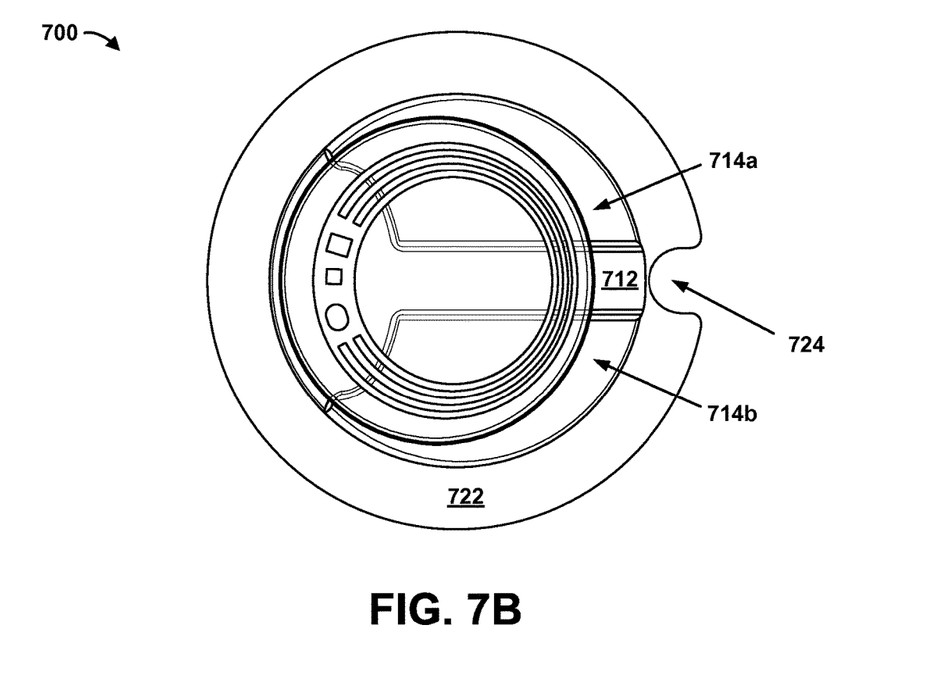
FIG. 7B illustrates a top view of the example apparatus of FIG. 7A, according to an example embodiment.

FIG. 7A illustrates yet another example apparatus 700 that includes a mounting structure 710 having one or more indentations, according to an example embodiment. FIG. 7B illustrates a top view of the example apparatus 700 of FIG. 7A, according to an example embodiment. In some examples, the apparatus 700 may be configured to removably mount a device 740 similar to the device 100 of the FIGS. 1A-1D using a method such as the method 200 of FIG. 2. The structure, operation, and composition of the apparatus 700 may be similar to the apparatus 300 of FIG. 3. For example, the apparatus 700 includes the mounting structure 710, a base structure 720, and a support structure 730 similar, respectively, to the mounting structure 310, the base structure 320, and the support structure 330 of the apparatus 300.

Additionally, for example, the mounting structure 710 includes a convex mounting surface 712 configured to removably mount at least a portion of a concave surface of the device 740, similarly to the convex mounting surface 312 in FIGS. 3A-3B. The support structure 730 may be configured to align the mounting structure 710 at a given angle 732 similarly to the given angle 332 of the apparatus 300. For example, when a concave surface of the device 740 is mounted on the mounting structure 710, a target area on a convex surface of the device 740 opposite the concave surface may be substantially parallel to a flat surface 722 based on the given angle 732. Similarly to the apparatus 400 of the FIG. 4, in some examples, indentations 714a-b may correspond to an omitted portion of a spherical surface that corresponds to the concave surface of the device 740. For example, the spherical surface may correspond to the convex mounting surface 312 of FIGS. 3A-3B, and the indentations 714a-b may correspond to an omitted portion of the mounting structure 310 such that the convex mounting surface 712 has a curvature that corresponds to a portion of the concave surface of the device 740.

Additionally, in some examples, the indentations 714a-b may be configured to accommodate a support for mounting and/or unmounting the device 740. Additionally, for example, the indentations 714a-b may reduce friction and/or van der Waals forces between the device 740 and the convex mounting surfaces 712. As illustrated in FIGS. 7A-7B, for example, the convex mounting surface 712 may correspond to at least a portion of the concave surface of the device 740 to provide support for the device 740 when mounted to the mounting structure 710.

In some examples, a shape of the indentations 714a-b may be indicative of the target area on the device 740. For example, as illustrated in FIG. 7B, the convex mounting surface 712 may correspond to a T-shape due to the shape of the indentations 714a-b, where the top of the T-shape may indicate the target area that is substantially parallel to the flat surface 722. Although not illustrated in FIG. 7B, the shape of the indentations 714a-b may also be utilized for aligning the device 740 when mounting the device 740 onto the mounting structure 710. For example, the shape of the indentations 714a-b may be indicative of features included in the device 740 (e.g., shape of the substrate 120 of the device 100 in FIGS. 1A-1D).

Within examples herein, an apparatus such as the apparatuses 300, 400, 500, and/or 700 may be configured to removably mount a concave surface of a device such as the device 100 such that a target area on a convex surface of the device opposite the concave surface is substantially parallel to a flat surface of a base structure of the apparatus. Thus, in these examples, liquid deposition on the target area may allow the target area to hold a volume of liquid when the device is mounted and avoid flow away of the volume of liquid due to gravity.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. An apparatus comprising:
a mounting structure having a convex mounting surface that corresponds to a concave surface of a device, wherein the device has a convex surface opposite the concave surface, and wherein the convex mounting surface has an edge defined by an indentation that prevents contact between the convex mounting surface and a portion of the concave surface of the device when the device is mounted on the mounting structure;
a base structure that has a flat surface; and
a support structure coupled to the base structure and the mounting structure, wherein the support structure aligns the mounting structure at a given angle such that a target area on the convex surface of the device is substantially parallel to the flat surface of the base structure when the device is mounted on the mounting structure, and wherein the target area is located between an edge of the convex surface of the device and a center of the convex surface of the device.

2. The apparatus of claim 1, wherein the indentation accommodates a support for supporting the concave surface of the device during mounting and unmounting of the device.

3. The apparatus of claim 2, wherein the indentation maintains the device in a given position on the mounting structure.

4. The apparatus of claim 2, wherein a shape of the indentation aligns with a shape of one or more features in the device.

5. The apparatus of claim 2, wherein the indentation reduces friction and van der Waals forces between the device and the mounting structure.

6. The apparatus of claim 1, further comprising a holder that removably mount the base structure such that the base structure is aligned in a given orientation when the base structure is mounted on the holder.

7. The apparatus of claim 6, wherein the holder includes a ridge and the base structure includes a cavity, wherein the ridge is received in the cavity when the base structure is mounted on the holder.

8. The apparatus of claim 1, wherein the target area holds a volume of liquid when the device is mounted on the mounting structure such that the target area is substantially parallel to the flat surface of the base structure.

9. The apparatus of claim 1, wherein the mounting structure includes an alignment mark that corresponds to the target area on the device.

10. A method comprising:
mounting, on a convex mounting surface of a mounting structure, a concave surface of a device, wherein the mounting structure is coupled to a support structure at a given angle, wherein the device has a convex surface opposite the concave surface, and wherein the convex mounting surface has an edge defined by an indentation that prevents contact between the convex mounting surface and a portion of the concave surface of the device responsive to the mounting; and aligning, based on the device being mounted on the convex mounting surface of the mounting structure and the mounting structure being coupled to the support structure at the given angle, a target area on the convex surface of the device such that the target area is substantially parallel to a flat surface of a base structure that is also coupled to the support structure, wherein the target area is located between an edge of the convex surface of the device and a center of the convex surface of the device.

11. The method of claim 10, wherein the indentation accommodates a support for supporting the concave surface of the device during mounting and unmounting of the device.

12. The method of claim 11, wherein the indentation maintains the device in a given position on the mounting structure.

13. The method of claim 11, wherein a shape of the indentation aligns with a shape of one or more features in the device.

14. The method of claim 11, wherein the indentation reduces friction and van der Waals forces between the device and the mounting structure.

15. A system comprising:
a device having a concave surface and a convex surface opposite the concave surface;
a mounting structure having a convex mounting surface that corresponds to the concave surface of the device, wherein the convex mounting surface has an edge defined by an indentation that prevents contact between the convex mounting surface and a portion of the concave surface of the device when the device is mounted on the mounting structure;
a base structure that has a flat surface; and
a support structure coupled to the base structure and the mounting structure, wherein the support structure aligns the mounting structure at a given angle such that a target area on the convex surface of the device is substantially parallel to the flat surface of the base structure when the device is mounted on the mounting structure, wherein the target area is located between an edge of the convex surface of the device and a center of the convex surface of the device.

16. The system of claim 15, wherein the indentation accommodates a support for supporting the concave surface of the device during mounting and unmounting of the device.

17. The system of claim 16, wherein the indentation maintains the device in a given position on the mounting structure.

18. The system of claim 16, wherein a shape of the indentation aligns with a shape of one or more features in the device.

19. The system of claim 16, wherein the indentation reduces friction and van der Waals forces between the device and the mounting structure.

20. The system of claim 15, further comprising a holder that removably mounts the base structure such that the base structure is aligned in a given orientation when the base structure is mounted on the holder.

* * * * *